United States Patent [19]

Herrera

[11] Patent Number: Plant 6,989

[45] Date of Patent: Aug. 15, 1989

[54] CHRYSANTHEMUM PLANT NAMED DARK RED SIMONA

[75] Inventor: Camilo Herrera, Bogota, Colombia

[73] Assignee: Whitefield Corporation, Panama

[21] Appl. No.: 250,541

[22] Filed: Sep. 29, 1988

[51] Int. Cl.[4] ..... A01H 5/00

[52] U.S. Cl. ..... Plt./82

[58] Field of Search ..... Plt./82

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Dark Red Simona particularly characterized as to uniqueness by the combined characteristics of flat capitulum form; decorative capitulum type; greyed-red ray floret color; diameter across face of capitulum of up to 9 cm at maturity; uniform 10 week photoperiodic flowering response to short days; tall plant height when grown single stem; 18 to 33 cm peduncles on open, normally terminal sprays; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Dark Red Simona.

Dark Red Simona is a spontaneous mutation of the unpatented cultivar Red Simona, and was selected to expand the color range of the parental variety. Dark Red Simona was discovered and selected as one flowering plant within a flowering block of Red Simona by Camilo Herrera in May of 1985, in a controlled environment at Jardines de los Andes, Madrid Cundinamarca, Colombia, South America.

The first act of asexual reproduction of Dark Red Simona was accomplished when vegetative cuttings were taken from the initial selection in August of 1985 in a controlled environment at Jardines de los Andes, Madrid Cundinamarca, Columbia, South America, by technicians working under formulations established and supervised by Camilo Herrera.

Horticultural examination of controlled flowerings of successive plantings has shown that the unique combination of characteristics as herein disclosed for Dark Red Simona are firmly fixed and are retained through successive generations of asexual reproduction.

Dark Red Simona has not been observed under all possible environmental conditions. The phenotype may vary significantly with variations in environment such as temperature, light intensity, and daylength.

The following observations, measurements and comparisons describe plants grown at Jardines de los Andes, Madrid Cundinamarca, Columbia, South America, under greenhouse conditions which approximate those generally used in commercial greenhouse practice. Flowering plant material was sent from Colombia to Salinas, Calif. for observations, measurements and color readings.

The following traits have been repeatedly observed and are determined to be basic characteristics of Dark Red Simona, which, in combination, distinguish this chrysanthemum as a new and distinct cultivar:

1. Flat capitulum form.
2. Decorative capitulum type.
3. Greyed-red floret color.
4. Diameter across face of capitulum up to 9 cm at maturity.

5. Uniform ten week photoperiodic flowering response to short days.
6. Peduncle length ranging from 18 to 33 cm.
7. Tall plant height, requiring one long day week prior to short days to attain a flowered plant height of 95 to 105 cm for year-round flowerings.
8. Excellent tolerance to low temperatures for bud initiation and flower development.

The accompanying photographic drawings show typical inflorescence and leaf characteristics of Dark Red Simona, with the colors being as nearly true as possible with illustrations of this type. Sheet 1 is a color photograph of Dark Red Simona grown as a single stem cut spray. Sheet 2 is a black and white photograph of three views of the inflorescence of Dark Red Simona. Sheet 3 is a black and white photograph showing the upper and under sides of the leaves of Dark Red Simona at three stages of development (mature, intermediate and immature).

Of the commercial cultivars known to the inventor, the most similar in comparison to Dark Red Simona is the parent cultivar Red Simona. All traits of Dark Red Simona are similar to those of Red Simona, except the color of ray florets. The color of ray florets of Dark Red Simona is darker and more red than those of Red Simona.

In the following description, color references are made to The Royal Horticultural Society Colour Chart. The exact colors for corolla of ray florets are not precisely represented in The Royal Horticultural Society Colour Chart, and the colors given are the closest to the actual color of Dark Red Simona. The color values were determined in Salinas, Calif. on Aug. 13, 1987.

Classification:

*Botanical.*—*Dendranthema grandiflora* cv Dark Red Simona.

*Commercial.*—Decorative cut spray mum.

INFLORESCENCE

A. Capitulum:

*Form.*—Flat.

*Type.*—Decorative.

*Diameter across face.*—Up to 9 cm at maturity.

B. Corolla of ray florets:

*Color* (*general tonality from a distance of three meters*).—Greyed-red.

*Color* (*upper surface*).—Closest to 179A.

*Color* (*under surface*).—179C, streaked with 179B.

*Shape.*—Straight, concave, pointed.

C. Corolla of disc florets:

*Color* (*mature*).—3A.

*Color* (*immature*).—154B. There are very few disc florets, which are covered by the ray florets at all stages of maturity.

D. Reproductive organs:

*Androecium.*—Present on disc florets only; very scant pollen.

*Gynoecium.*—Present on both ray and disc florets.

PLANT

A. General appearance:

*Height.*—Tall; 95 to 105 cm as a single stem cut mum with 7 long days prior to short days.

B. Foliage:

*Color* (*upper surface*).—147A.

*Color* (*under surface*).—147B to 147C.

*Shape.*—Deeply lobed and serrated.

I claim:

1. A new and distinct Chrysanthemum plant named Dark Red Simona, as described and illustrated.

* * * * *

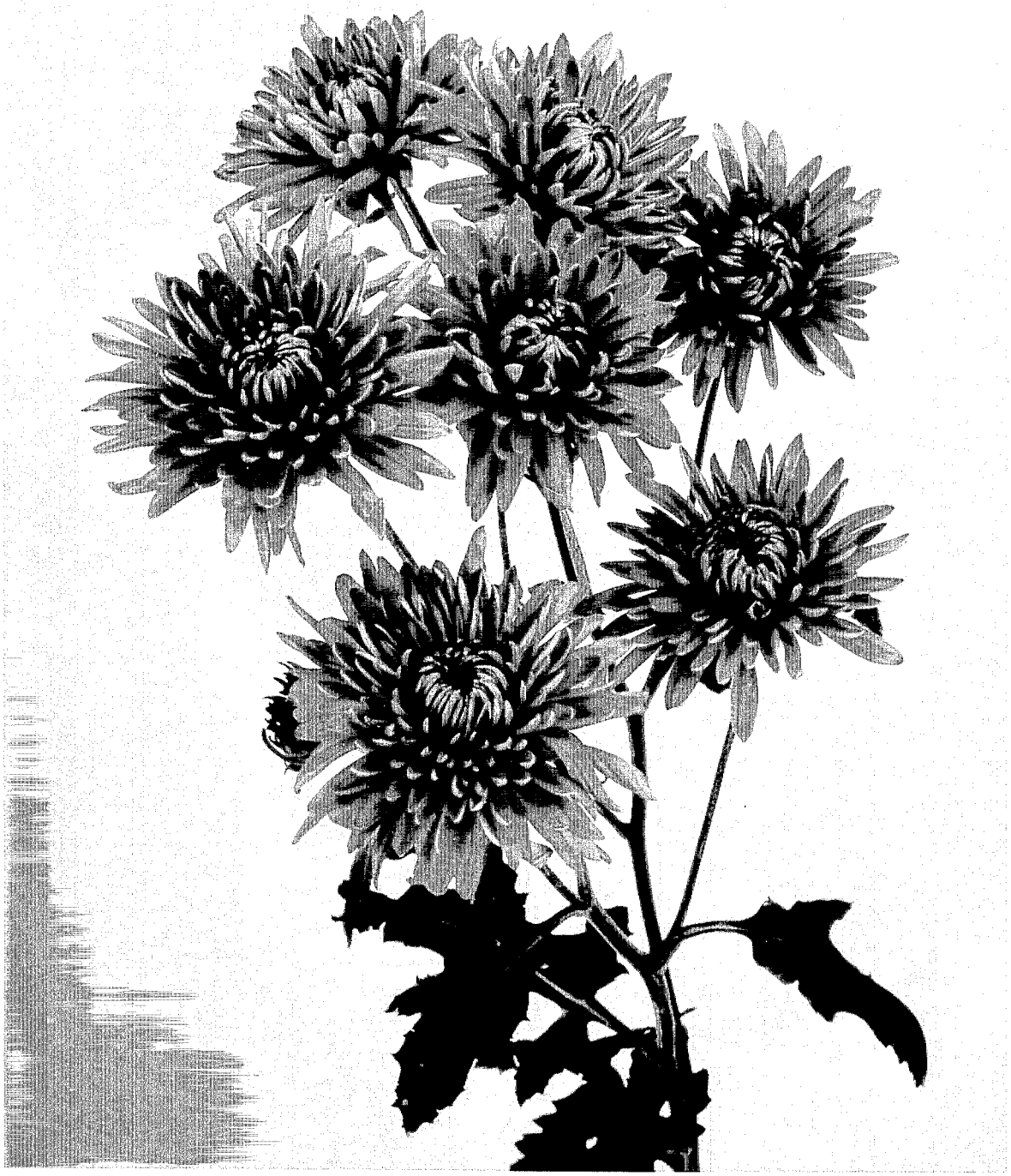

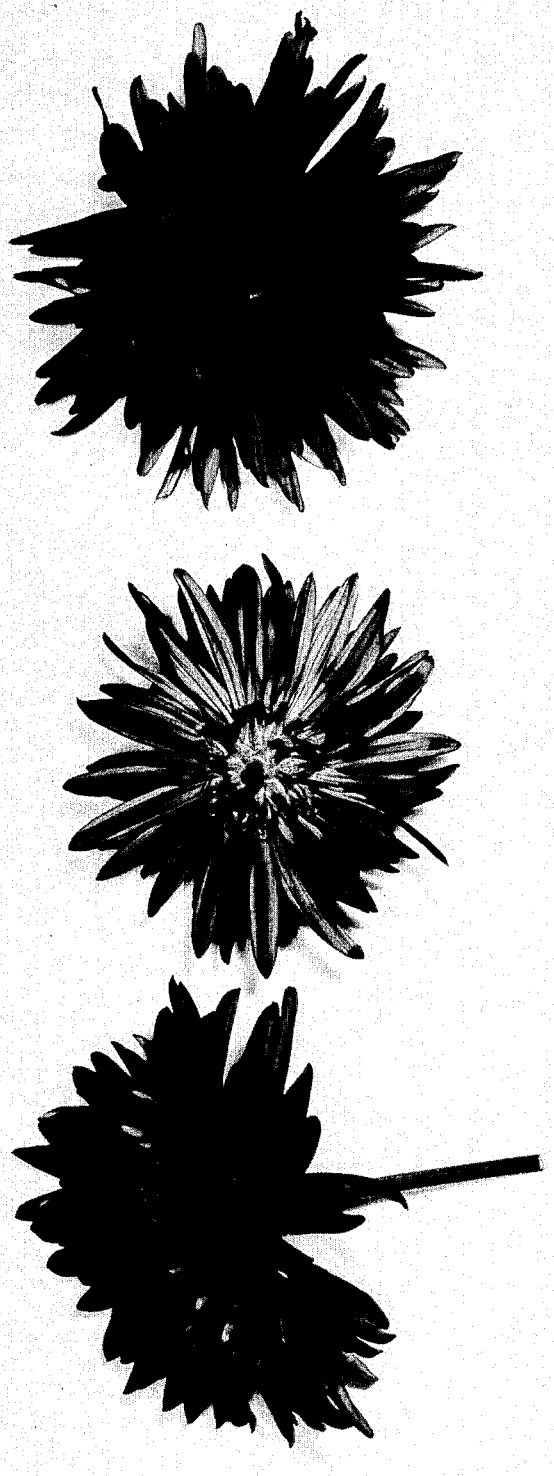

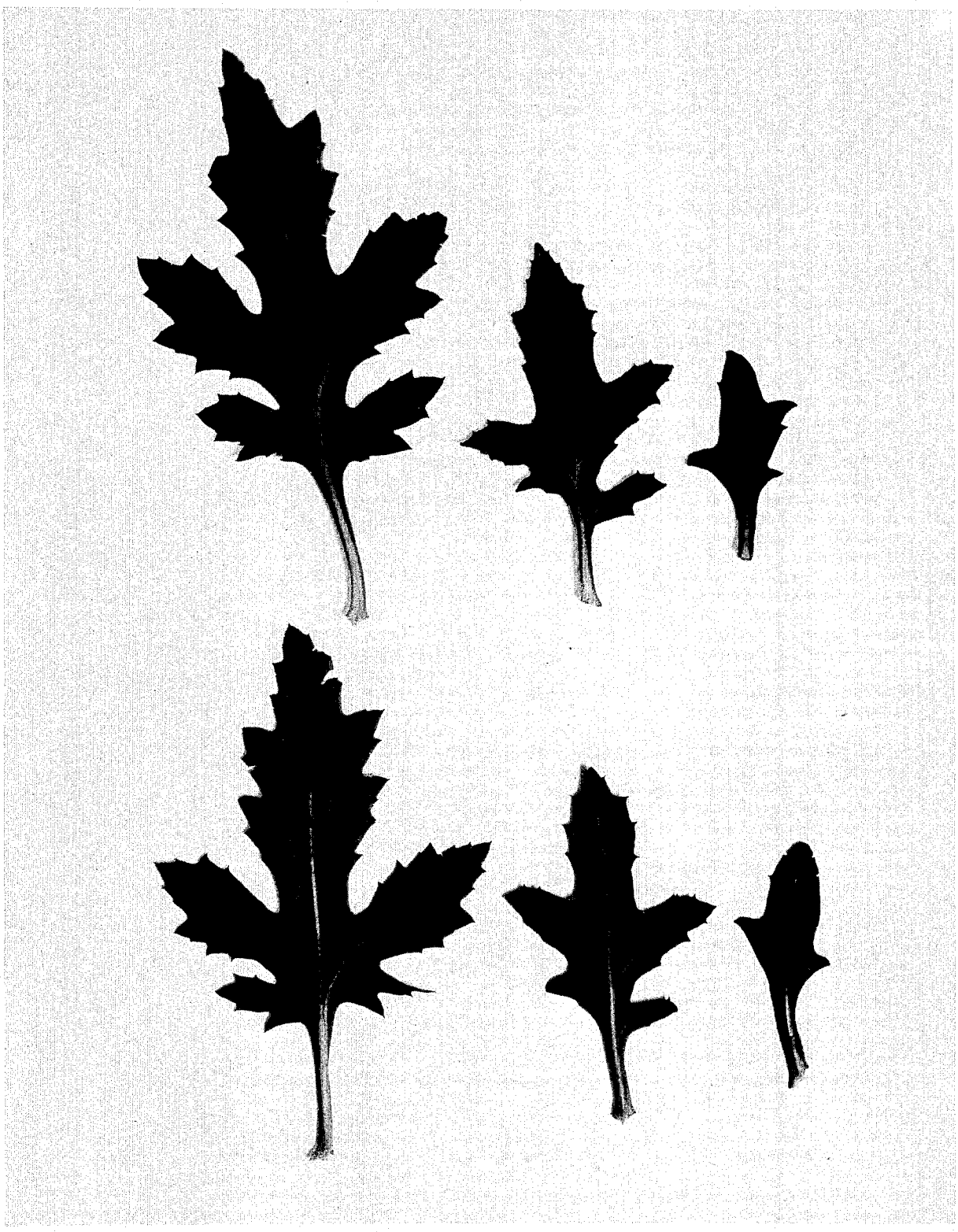

UNITED STATES PATENT AND TRADEMARK OFFICE

CERTIFICATE OF CORRECTION

PATENT NO. : Plant 6,989

DATED : August 15, 1989

INVENTOR(S) : Camilo Herrera

It is certified that error appears in the above—identified patent and that said Letters Patent is hereby corrected as shown below:

Column 1, line 17, "Columbia" should be changed to --Colombia--.

Column 1, line 31, "Columbia" should be changed to --Colombia--.

Signed and Sealed this

Second Day of April, 1991

*Attest:*

HARRY F. MANBECK, JR.

*Attesting Officer*

*Commissioner of Patents and Trademarks*